US008455661B2

(12) United States Patent
Veige et al.

(10) Patent No.: US 8,455,661 B2
(45) Date of Patent: Jun. 4, 2013

(54) CATALYSTS CONTAINING N-HETEROCYCLIC CARBENES FOR ENANTIOSELECTIVE SYNTHESIS

(75) Inventors: Adam Steven Veige, Gainesville, FL (US); Mathew S. Jeletic, Gainesville, FL (US); Roxy J. Lowry, Chapel Hill, NC (US); Khalil A. Abboud, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 474 days.

(21) Appl. No.: 12/527,635

(22) PCT Filed: Feb. 15, 2008

(86) PCT No.: PCT/US2008/054137
§ 371 (c)(1),
(2), (4) Date: Jan. 20, 2010

(87) PCT Pub. No.: WO2008/101197
PCT Pub. Date: Aug. 21, 2008

(65) Prior Publication Data
US 2010/0292465 A1    Nov. 18, 2010

Related U.S. Application Data

(60) Provisional application No. 60/890,484, filed on Feb. 18, 2007, provisional application No. 60/985,205, filed on Nov. 3, 2007.

(51) Int. Cl.
| | | |
|---|---|---|
| *C07F 15/00* | (2006.01) |
| *C07F 13/00* | (2006.01) |
| *C07F 11/00* | (2006.01) |
| *C07D 239/24* | (2006.01) |
| *C07D 235/06* | (2006.01) |
| *C07D 235/04* | (2006.01) |
| *C07D 233/58* | (2006.01) |
| *C07D 233/56* | (2006.01) |
| *C07D 487/14* | (2006.01) |

(52) U.S. Cl.
USPC ............ 548/262.2; 548/266.4; 548/300.1; 548/304.4; 548/304.7; 544/242; 556/136; 556/140; 556/143; 556/112; 556/58

(58) Field of Classification Search
USPC ......... 548/262.2, 266.4, 300.1, 304.4, 304.7; 544/242; 556/136, 140, 143, 112, 58
See application file for complete search history.

(56) References Cited

U.S. PATENT DOCUMENTS

| | | |
|---|---|---|
| 4,331,818 A | 5/1982 | Riley |
| 4,397,787 A | 8/1983 | Riley |
| 5,739,396 A | 4/1998 | Trost et al. |
| 6,172,249 B1 | 1/2001 | Berens et al. |
| 6,297,387 B1 | 10/2001 | Antognazza et al. |
| 6,333,291 B1 | 12/2001 | Yokozawa et al. |
| 6,987,202 B2 | 1/2006 | Shimizu et al. |
| 7,078,568 B2 | 7/2006 | Shimizu et al. |
| 2002/0177710 A1 | 11/2002 | Grubbs et al. |

FOREIGN PATENT DOCUMENTS
WO    WO 02/08169    1/2002

OTHER PUBLICATIONS

Clyne et al. Organic Letters, vol. 2(8), 1125-1128, 2000.*
Allinger, N.L. et al., *Organic Chemistry Second Edition*, 1976, pp. 374-377, Worth Publishers, Inc. New York, NY.
Huheey, J.E., *Inorganic Chemistry, Principles of Structure and Reactivity, Second Edition*, 1978, pp. 343, 387-388, 430-431, Harper & Row Publishers, Inc., New York, NY.
Katritzky, A. R. et al., "An improved method for the N-alkylation of benzotriazole and 1,2,4-triazole," *Recueil des Travaux Chimiques des Pays-Bas*, 1991, pp. 369-373, vol. 10, Issue 9.
Lagowski, J.J., *Modern Inorganic Chemistry*, 1973, pp. 629-630, Marcel Dekker, Inc., New York, NY.
Streitwieser, A. et al., *Introduction to Organic Chemistry, Fourth Edition*, 1992, pp. 178-181, Macmillan Publishing Company, New York, NY.
Diez-Gonzalez, S. et al., "N-Heterocyclic Carbenes in Late Transition Metal Catalysis," *Chem. Rev.*, 2009, pp. 3612-3676, vol. 109.
Jeletic, M.S. et al., "New iridium and rhodium chiral di-*N*-heterocyclic carbene (NHC) complexes and their application in enantioselective catalysis," *Dalton Trans.*, 2009, pp. 2764-2776.
Jeletic, M.S., et al., A new chiral di-*N*-heterocyclic carbene (NHC) cyclophane ligand and its application in palladium enantioselective catalysis, *Dalton Trans.*, 2010, pp. 6392-6394, vol. 39.
Jeletic, M.S. et al., "Chemical Exchange Saturation Transfer (CEST) as a Tool to Measure Ligand Flexibility of Chelating Chiral Di-N-heterocyclic Carbene Complexes," *Organometallics* 2011, pp. 6034-6043, vol. 30.
Lowry, R.J. et al., "The next generation of C2-symmetric ligands: A di-*N*-heterocyclic carbene (NHC) ligand and the synthesis and X-ray characterization of mono- and dinuclear rhodium(I) and iridium(I) complexes," *Polyhedron*, 2010, pp. 553-563, vol. 29.
Wang, F. et al., "Chiral NHC-metal-based asymmetric catalysis," *Coordination Chemistry Reviews*, 2012, pp. 804-853, vol. 256.

* cited by examiner

*Primary Examiner* — Venkataraman Balasubramanian
(74) *Attorney, Agent, or Firm* — Saliwanchik, Lloyd & Eisenschenk

(57) ABSTRACT

Novel N-heterocyclic carbene ligand precursors, N-heterocyclic carbene ligands and N-heterocyclic metal-carbene complexes are provided. Metal-carbene complexes comprising N-heterocyclic carbene ligands can be chiral, which are useful for catalyzing enantioselective synthesis. Methods for the preparation of the N-heterocyclic carbene ligands and N-heterocyclic metal-carbene complexes are given.

9 Claims, 4 Drawing Sheets

CATALYSTS CONTAINING N-HETEROCYCLIC CARBENES FOR ENANTIOSELECTIVE SYNTHESIS

CROSS-REFERENCE TO RELATED APPLICATIONS

The present application is the U.S. National Stage Application of International Patent Application No. PCT/US2008/054137, filed on Feb. 15, 2008, which claims the benefit of U.S. Provisional Application Ser. No. 60/890,484, filed Feb. 18, 2007, and U.S. Provisional Application Ser. No. 60/985,205, filed Nov. 3, 2007, all of which are hereby incorporated by reference herein in their entirety, including any figures, tables, and drawings.

FIELD OF THE INVENTION

The present invention relates to N-heterocyclic carbene ligands and transition metal complexes including such ligands. The subject invention also relates to catalysts for metal catalyzed and N-heterocyclic organocatalyzed enantioselective synthesis.

BACKGROUND OF THE INVENTION

When chemical reactions yield chiral compounds, the separation of enantiomers can be extremely important. In the pharmaceutical industry, for example, oftentimes one enantiomer of a compound provides a beneficial effect while the other enantiomer causes harmful side effects. Thus, "single enantiomer" drugs are often highly desirable.

Unfortunately, it is sometimes difficult to obtain a composition that consists only of one enantiomer of a chiral compound. For example, because of the similarity of the physical properties of the enantiomers, it can be very difficult to isolate a single enantiomer from a racemic mixture.

One method of producing only one enantiomer is called asymmetric synthesis, or chiral synthesis. A strategy that is often attempted in asymmetric synthesis is to use a chiral ligand. The ligand complexes to the starting materials and physically blocks the other trajectory for attack, leaving only the desired trajectory open. This leads to production of only one type of enantiomer of the product.

A class of chiral substances that are typical of the prior art is chiral phosphines, in combination with compounds of rhodium or ruthenium. These complexes work as catalysts for enantioselective synthesis in certain types of reactions, including hydrogenation of functionalized alkenes.

Chiral phosphine ligands and their production and use are described in, for example, U.S. Pat. Nos. 7,078,568 and 6,987,202 to Shimizu et al., 6,333,291 to Yokozawa et al., 6,297,387 to Antognazza et al., 6,172,249 to Berens et al., and 4,397,787 and 4,331,818 to Riley, all of which are hereby incorporated by reference.

These chiral phosphine ligand metal complexes are used for catalysts in the pharmaceutical industry. Catalysts are very important to speed up and sometimes even initiate chemical reactions. As such, there is always a need for cheaper, cleaner, and more stable catalysts that provide high yields. Specifically, in the context of the current invention, there is a need for catalysts that can be used to promote reactions leading to the synthesis of a desired single enantiomer compound.

BRIEF SUMMARY OF THE INVENTION

The subject invention provides new and advantageous ligands. The ligands of the subject invention contain at least two chiral centers and can be resolved into enantionmerically pure forms that can be used to form metal complexes for catalyzed synthesis, including enantioselective synthesis. Specifically exemplified herein are molecules that can provide one or two N-heterocyclic carbene sites for complexation as a ligand. There are two chiral centers common to all N-heterocyclic carbene ligands of the invention at the 9 and 10 positions of trans-9,10-substituted-ethanoanthracene. The trans-9,10-substituted-ethanoanthracene portion of the molecule acts as a framework moiety for the disposition of the N-heterocyclic carbene ligands and other ligands or substituents of the N-heterocyclic carbene ligands.

In one embodiment, N-heterocyclic carbene ligands are combined with a metal to form a metal-carbene complex that can include other achiral or chiral ligands. The metal of the metal-carbene complex include transition metals such as Rh, Ir, Pd, Pt and Ru. The metal-carbene complex may be either bimetallic or monometallic, where each metal can have one or two N-heterocyclic carbenes attached to the metal. The two N-heterocyclic carbenes of a bis-N-heterocyclic carbene ligand can be complexed to a single metal or each N-heterocyclic carbene can be complexed to different metals. The oxidation state of the metal can vary as is appropriate for complexes of the metal as is understood by those skilled in the art. One or more anions can be present as counterions to the metal-carbene complexes.

In another embodiment, a method is provided for the preparation of the N-heterocyclic carbene ligand precursors from trans-9,10-substituted-ethanoanthracenes. The method involve transformations of a trans-9,10-substituted-ethanoanthracene by the addition to or formation of one or two N-heterocyclic groups. From these ligand precursors the N-heterocyclic carbene ligands can be prepared by reaction with a non-nucleophilic base.

In another embodiment, a method is provided for formation of metal-carbene complexes by combining an N-heterocyclic carbene ligand with a metal salt. The metal salt can be uncomplexed or complexed, and the resulting metal complex can be a monometallic his-carbene complex, a monometallic mono-carbene complex or a dimetallic his-carbene complex, depending on the starting N-heterocyclic carbene ligand and metal.

The N-heterocyclic carbene ligands of the subject invention are less toxic, more stable, and potentially less expensive than the current phosphine ligands. Additionally, the carbene ligands of the present invention can be formed in higher yields than phosphine ligands. Moreover, the metal-carbene complexes including the N-heterocyclic carbene ligands of the subject invention can catalyze a wider variety of reactions than metal complexes containing phosphine ligands.

DETAILED DESCRIPTION OF THE INVENTION

Figure 1:
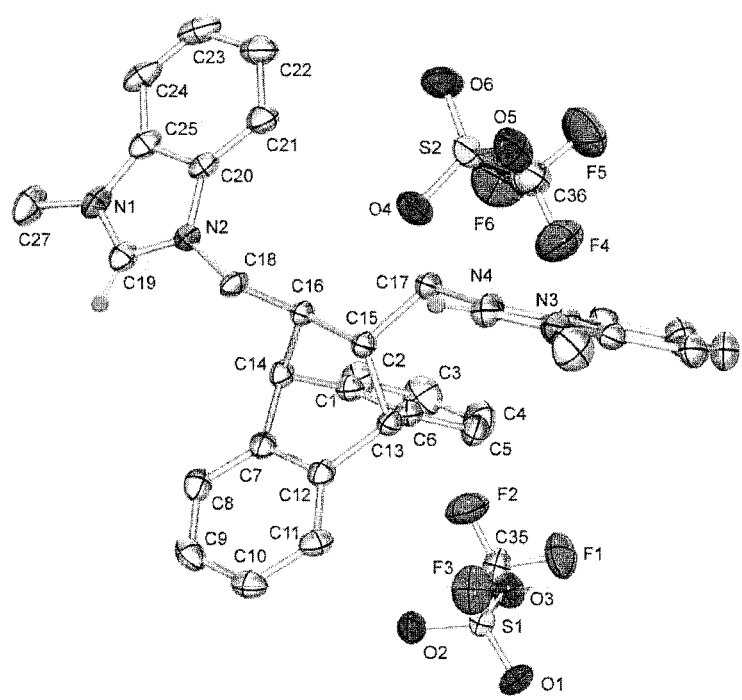
FIG. 1 shows the molecular structure of trans-9,10-dihydro-9,10-ethanoanthracene-11,12-di-1-methylbenzimidazolium triflate as determined by X-ray crystallography.

The present invention is directed to N-heterocyclic carbene ligand precursors, N-heterocyclic carbene ligands, metal-carbene complexes from these N-heterocyclic carbene ligands, and methods to prepare the N-heterocyclic carbene ligand precursors, N-heterocyclic carbene ligands, and the metal-carbene complexes. The N-heterocyclic carbene ligand precursors, N-heterocyclic carbene ligands, and metal-carbene complexes are illustrated within this disclosure as a single enantiomer, however, it is to be understood that the opposite enantiomer and the racemic mixtures of the illustrated enantiomer are also embodiments of this invention. Ionic species are herein illustrated as ion pairs, which are not intended to infer that these ionic species can not exist under the appropriate conditions as free ions, complexed ions or solvated ions. All of these ionic forms are possible under appropriate conditions for the inventive N-heterocyclic carbene ligand precursors and metal-carbene complexes. Additionally, cations in the N-heterocyclic carbene ligand precursors are generally illustrated as a localized ion, but are generally delocalized cations, as can be appreciated by those skilled in the art. Although the N-heterocyclic carbene ligands according to the invention are defined as carbenes, the N-heterocyclic carbene ligand may exist having carbene equivalents, for example, as an enetetramine rather than as formal carbenes, and these equivalent forms are within the definition of a carbene ligand according to the invention. The N-heterocyclic carbene ligands can exist in solution as formed and used without isolation from reagents and solvent.

These metal-carbene complexes can be used to catalyze a wide variety of synthetic transformations, and can be used as catalysts in enantioselective synthesis to generate products with a high enantiomeric excess, in some transformations allowing the isolation of a single enantiomer of a chiral product. The enantioselective synthesis can be used for the synthesis of optically enriched and optically pure compounds, where the isolation of a pure enantiomer can result in a product with superior properties over that of a racemic mixture or partially resolved mixture of enantiomers, as, for example, in the case of many pharmaceuticals.

Advantageously, the bis-N-heterocyclic carbene ligands of the subject invention are stronger donors of σ-electrons than even the most electron-rich phosphines. They are also much less labile than phosphine ligands and thus less susceptible to catalyst degradation. The N-heterocyclic carbene ligands described herein are also less toxic and potentially less expensive to produce than phosphine ligands, and they can be electronically and sterically fine-tuned. N-heterocyclic carbene ligands provide a planar environment in a metal complex therefrom, as opposed to the conical environment of typical phosphine ligands complexed to a metal.

The N-heterocyclic carbene ligand precursor of the present invention is shown in Formula I:

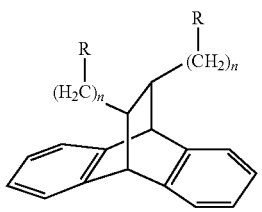

where n is 0 or 1:
where each R is independently:

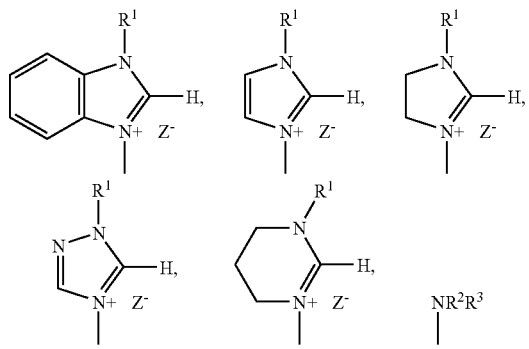

where at least 1 R is other than $NR^2R^3$;

where $R^1$, $R^2$, and $R^3$ are independently: H; $C_1$ to $C_{18}$ straight, branched, or multiply branched alkyl; benzyl; substituted benzyl; phenyl; substituted phenyl; napthyl; substituted napthyl; pyridyl; substituted pyridyl; quinolyl; substituted quinolyl; or pentafluorobenzyl; and in combination $R^2R^3$ can be $=CHR^1$; and where $Z^-$ is $Cl^-$, $Br^-$, $I^-$, $PF_6^-$, $SbF_6^-$, $^-OSO_2CF_3$, $^-OSO_2C_6H_5$ or $^-OSO_2C_6H_4-R^4$, where $R^4$ is an alkylene or oxyalkylene unit bridged with a polymer or polymeric resin. Substituted, branched, and multiply branched substituents can be achiral, chiral, enantiomerically enriched, or racemic. Substitution or branching can occur at any carbon of the base substituent. The position of substitution to a multi carbon containing $R^1$, $R^2$, and $R^3$ can be at any carbon containing an H in the base structure as would be recognized by one skilled in the art. Substituted can mean mono or multiply substituted where the substituent can be any alkyl, vinyl, alkenyl, alkynyl, or aryl group. Any N-heterocyclic carbene ligand precursor can exist as a racemic mixture, as a partially or totally resolved enantiomer, or as one or more of multiple possible diastereomers. Any carbon-hydrogen bond other than that of the carbon between the two nitrogen atoms of R can be replaced with an alkylene or oxyalkylene unit bridging the N-heterocyclic carbene ligand precursor to a polymer or polymeric resin.

In one embodiment, the N-heterocyclic carbene ligand precursor is a bis-N-heterocyclic carbene ligand precursor, as shown in Formula II, which is a subset of Formula I where n is 1:

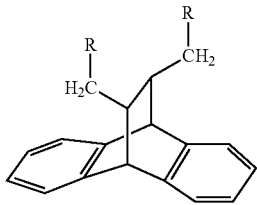

(II)

where R is independently:

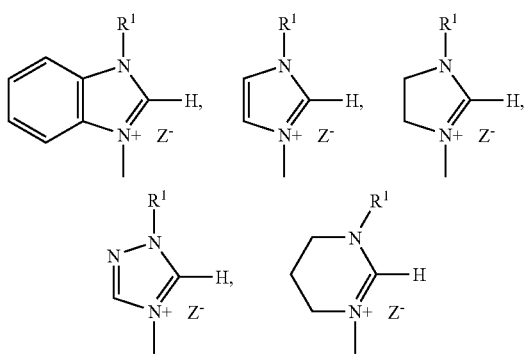

where $R^1$ is: H; $C_1$ to $C_{18}$ straight, branched, or multiply branched alkyl; benzyl; substituted benzyl; phenyl; substituted phenyl; napthyl; substituted napthyl; pyridyl; substituted pyridyl; quinolyl; substituted quinolyl; or pentafluorobenzyl; and where Z is $Cl^-$, $Br^-$, $I^-$, $PF_6^-$, $SbF_6^-$, $^-OSO_2CF_3$, $^-OSO_2C_6H_5$ or $^-OSO_2C_6H_4$—$R^4$, where $R^4$ is an alkylene or oxyalkylene unit bridged with a polymer or polymeric resin In another embodiment, the N-heterocyclic carbene ligand precursor is a bis-N-heterocyclic carbene ligand precursor, as shown in Formula III, which is a subset of Formula I where n is 0:

(III)

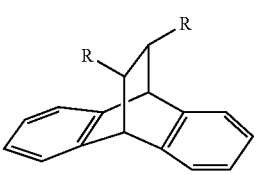

where R is independently:

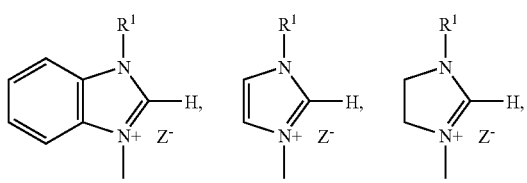

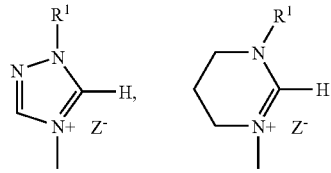

where $R^1$ is independently: H; $C_1$ to $C_{18}$ straight, branched, or multiply branched alkyl; benzyl; substituted benzyl; phenyl; substituted phenyl; napthyl; substituted napthyl; pyridyl; substituted pyridyl; quinolyl; substituted quinolyl; or pentafluorobenzyl;

where Z is $Cl^-$, $Br^-$, $I^-$, $PF_6^-$, $SbF_6^-$, $^-OSO_2CF_3$, $^-OSO_2C_6H_5$ or $^-OSO_2C_6H_4$—$R^4$, where $R^4$ is an alkylene or oxyalkylene unit bridged with a polymer or polymeric resin.

In another embodiment, the N-heterocyclic carbene ligand precursor is a mono-N-heterocyclic carbene ligand precursor, as shown in Formula IV, which is a subset of Formula I where n is 0:

(IV)

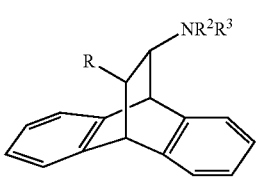

where R is:

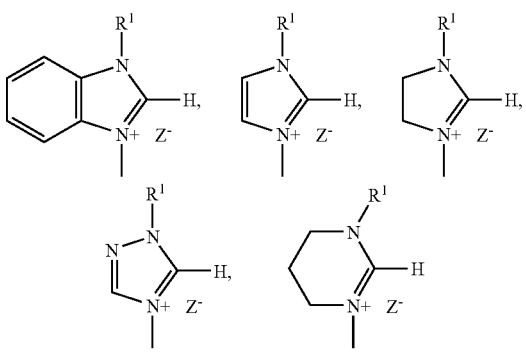

where $R^1$, $R^2$, and $R^3$ are independently: H; $C_1$ to $C_{18}$ straight, branched, or multiply branched alkyl; benzyl; substituted benzyl; phenyl; substituted phenyl; napthyl; substituted napthyl; pyridyl; substituted pyridyl; quinolyl; substituted quinolyl; or pentafluorobenzyl, or combined $R^2R^3$ can be =$CHR^1$; and where Z is $Cl^-$, $Br^-$, $I^-$, $PF_6^-$, $SbF_6^-$, $^-OSO_2CF_3$, $^-OSO_2C_6H_5$ or $^-OSO_2C_6H_4$—$R^4$, where $R^4$ is an alkylene or oxyalkylene unit bridged with a polymer or polymeric resin.

The N-heterocyclic carbene ligand precursor can exist as a single enantiomer or can be used as a racemic mixture, where an N-heterocyclic carbene metal complex ultimately formed from the N-heterocyclic carbene ligand precursor is to be resolved subsequently, or when the chiral properties of the metal complex are not to be exploited. The single enantiomer of the N-heterocyclic carbene ligand precursor can be prepared as a single enantiomer or resolved from a racemic mixture.

In one embodiment of the invention the N-heterocyclic carbene ligand precursor can be attached to a polymer or to a polymeric resin. Any carbon-hydrogen bond other than that of the carbon between the two nitrogen atoms of R in Formula I can be replaced with an alkylene or oxyalkylene unit bridging the N-heterocyclic carbene ligand precursor to a polymer or polymeric resin. The site of attachment to the polymer or polymeric resin can be via any site of substitution or branching in Formula I. The trans-9,10-substituted-ethanoanthracenes portion of the N-heterocyclic carbene ligand comprising molecules can be substituted at one or more of the available carbons with a hydrogen substituent on the aromatic rings.

In an embodiment of the invention where the N-heterocyclic carbene ligand precursor is attached to a polymer or to a polymeric resin, the polymer can be any soluble organic polymer or any cross-linked polymer resin. For example, the polymer can be any organic polymer commonly prepared by a step-growth or chain-growth mechanism. Exemplary polymers include: polystyrenes, polyacrylates, polymethacrylates, polyalkenes, polyesters, polyamides, polyethers, and polysiloxane. Polymeric resins can be any cross-linked organic polymer including polystyrene resins, acrylic resins, epoxy resins, and fluorocarbon resins. The N-heterocyclic carbene ligand precursor can be attached by an ionic bond where the anion, Z, of Formula I is an $^-OSO_2C_6H_4-R^4$ group, where $R^4$ is an alkylene or oxyalkylene unit bridged to a polymer or polymeric resin. In this manner, a cation exchange resin can be transformed into an N-heterocyclic carbene ligand comprising resin by ion exchange of an N-heterocyclic carbene ligand comprising molecule with a cation bound to the resin.

A method to synthesize N-heterocyclic carbene ligand precursors comprises the introducing one or two N-heterocyclic groups to a base containing at least two chiral centers but is not a meso compound. Commercially available trans-9,10-dihydro-9,10-ethanoanthracene compounds can become substituted with one or two N-heterocyclic groups without racemization of the 9 and 10 carbons. The introduction of the N-heterocyclic group can be carried out by a substitution reaction with the formation of a salt by mixing a bis-triflate ester, or other ester that can act as a good leaving group, from trans-9,10-dihydro-9,10-ethanoanthracene-11,12-dimethanol with an N-heterocycle, as is shown below in Example 2, for the reaction with 1-methylbenzimidazole. Alternately, the N-heterocyclic groups can be introduced by the formation of a heterocyclic from a trans-9,10-dihydro-9,10-ethanoanthracene-11,12-diamine by carrying out a cyclization reaction involving an amine of the trans-9,10-dihydro-9,10-ethanoanthracene-11,12-diamine. For example, as is shown below in Example 7, the N-heterocyclic carbene ligand precursor is formed by the cyclization reaction of trans-9,10-dihydro-9,10-ethanoanthracene-11,12-diamine with glyoxal followed by ammonium chloride and formaldehyde.

The synthesis can be carried out using a pure enantiomer of the starting trans-9,10-ethanoanthracene compound in the first step of the synthetic method. Alternately, enantiomers of the N-heterocyclic carbene ligand precursors can be resolved to yield a desired enantionmerically enriched or pure N-heterocyclic carbene ligand precursor and ultimately an enantionmerically enriched or pure N-heterocyclic metal-carbene complex. Resolution can be by any means, for example, chromatography of the racemic mixture using a chiral solvent and/or a chiral stationary phase. Resolution can be provided by kinetic means, such as in a reaction using an excess of the trans-9,10-ethanoanthracene compound and a limiting amount of one or more complementary reagents that are chiral or have been rendered effectively chiral by association or complexation of the reagent, or conversely the trans-9,10-ethanoanthracene compound, with a chiral auxiliary, or by using a chiral solvent to selectively lower the energy of the ground state or transition state in the reaction of one enantiomer of the starting material in a synthetic step.

In an embodiment of the invention, a method is given for the synthesis of an N-heterocyclic carbene ligand by the reaction of an N-heterocyclic carbene ligand precursor with a non-nucleophilic base, such as an alkali salt of a hindered amine. For example, potassium hexamethyldisilazane, as is shown below in Examples 3, for the formation of trans-9,10-dihydro-9,10-ethanoanthracene-11,12-bis(1-methylbenzimidazolidine-2-ylidine.

In one embodiment of the invention, the N-heterocyclic carbene ligand is a bis N-heterocyclic carbene as illustrated by Formula V for an enetetramine form or Formula VI as a bis-carbene:

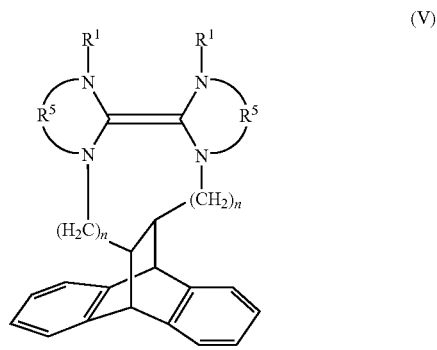

(V)

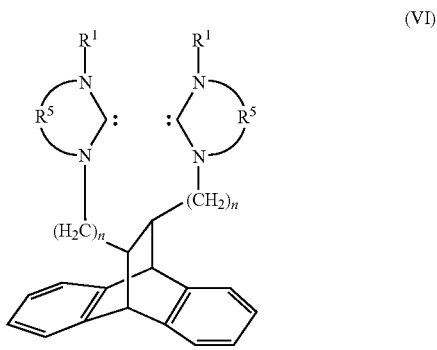

(VI)

where n is 0 or 1;
where $R^5$ is independently:

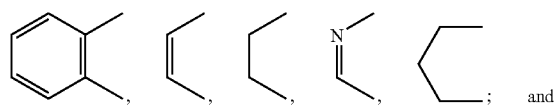

; and where $R^1$ groups are independently: H; $C_1$ to $C_{18}$ straight, branched, or multiply branched alkyl; benzyl; substituted benzyl; phenyl; substituted phenyl; napthyl; substituted napthyl; pyridyl; substituted pyridyl; quinolyl; substituted quinolyl; or pentafluorobenzyl. The position of substitution to a multi carbon $R^1$ can be at any carbon containing an H in the base structure as would be recognized by one skilled in the art. Substituted can mean mono or multiply substituted where the substituent can be any alkyl, vinyl, alkenyl, alkynyl, or aryl group. Any N-heterocyclic carbene ligand can exist as a racemic mixture, as a partially or totally resolved enantiomer, or as one or more of multiple possible diastereomers.

In another embodiment of the invention, the N-heterocyclic carbene ligand is a mono N-heterocyclic carbene, as illustrated by Formula VII.

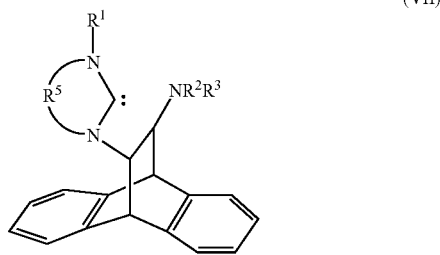

(VII)

where $R^5$ is:

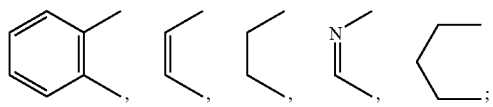

and where $R^1$, $R^2$ and $R^3$ groups are independently: H; $C_1$ to $C_{18}$ straight, branched, or multiply branched alkyl; benzyl; substituted benzyl; phenyl; substituted phenyl; napthyl; substituted napthyl; pyridyl; substituted pyridyl; quinolyl; substituted quinolyl; or pentafluorobenzyl. The position of substitution to a multi carbon $R^1$ can be at any carbon containing an H in the base structure as would be recognized by one skilled in the art. Substituted can mean mono or multiply substituted where the substituent can be any alkyl, vinyl, alkenyl, alkynyl, or aryl group. Any N-heterocyclic carbene ligand can exist as a racemic mixture, as a partially or totally resolved enantiomer, or as one or more of multiple possible diastereomers.

The N-heterocyclic carbene ligand can exist as a short lived intermediate where a metal-carbene complex is formed by a reaction in situ and where no free N-heterocyclic carbene ligand is isolated, or stored unisolated in a reaction mixture. Where mono N-heterocyclic carbene ligands are the intermediate, formation of the carbene and subsequent formation of the metal-carbene complex is frequently carried out in this manner.

The N-heterocyclic carbene ligand can be combined with a metal salt to form a metal-carbene complex. The metal-carbene complex can be a metal complexed with two N-heterocyclic carbene ligands of a bis-N-heterocyclic carbene ligand, a metal complexed with a single N-heterocyclic carbene ligand of a mono-N-heterocyclic carbene ligand, or two metals complexed to a bis-N-heterocyclic carbene ligand where each metal is complexed a single N-heterocyclic carbene. The coordination number of the metal can be 4-6. Many embodiments of the metal-carbene complexes of the present invention are directed to a 4-coordinate metal.

In one embodiment of the invention the metal-carbene complex is a monometallic bis N-heterocyclic carbene complex, as illustrated by Formula VIII:

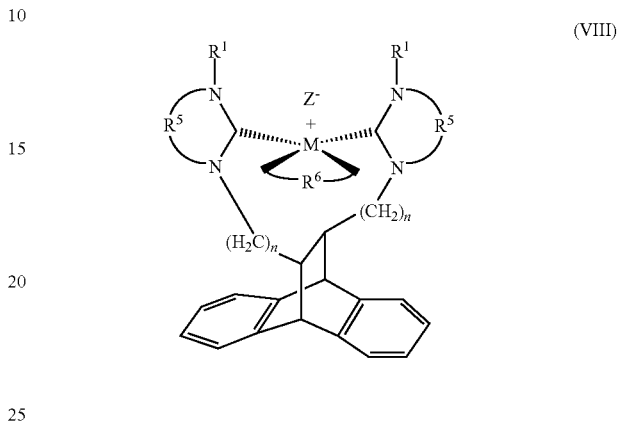

(VIII)

where n is 0 or 1;
where $R^5$ is independently:

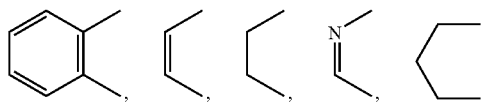

where $R^1$ groups are independently: H; $C_1$ to $C_{18}$ straight, branched, or multiply branched alkyl; benzyl; substituted benzyl; phenyl; substituted phenyl; napthyl; substituted napthyl; pyridyl; substituted pyridyl; quinolyl; substituted quinolyl; or pentafluorobenzyl;

where Z is Cl$^-$, Br$^-$, I$^-$, PF$_6^-$, SbF$_6^-$, $^-$OSO$_2$CF$_3$, $^-$OSO$_2$C$_6$H$_5$ or $^-$OSO$_2$C$_6$H$_4$—R$^4$, where $R^4$ is an alkylene or oxyalkylene unit bridged with a polymer or polymeric resin;

where M is Rh, Ir, Pd, Pt, Ru, or other transition metal; and where $R^6$ is an ancillary bidentate diene ligand selected from the group consisting of norbornene, substituted norbornene, 1,5-cyclooctadiene, and substituted 1,5-cyclooctadiene. Substituted, branched, and multiply branched substituents can be achiral, chiral, enantionmerically enriched, or racemic. Substitution or branching can occur at any carbon of the base substituent. The position of substitution to a multi carbon $R^1$ can be at any carbon containing an H in the base structure, as would be recognized by one skilled in the art Substituted can mean mono or multiply substituted where the substituent can be any alkyl, vinyl, alkenyl, alkynyl, or aryl group. Any N-heterocyclic carbene ligand can exist as a racemic mixture, as a partially or totally resolved enantiomer, or as one or more of multiple possible diastereomers.

In another embodiment of the invention the metal-carbene complex is a bimetallic bis-N-heterocyclic carbene complex, as illustrated by Formula IX:

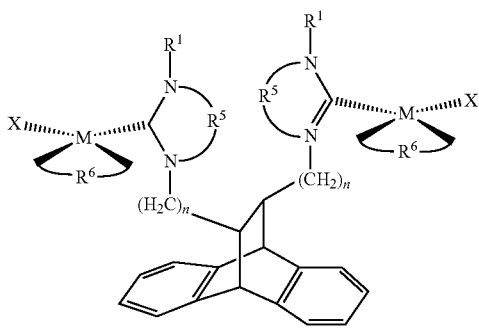

(IX)

where n is 0 or 1;

$R^5$ is independently:

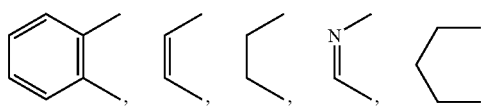

where $R^1$ groups are independently: H; $C_1$ to $C_{18}$ straight, branched, or multiply branched alkyl; benzyl; substituted benzyl; phenyl; substituted phenyl; napthyl; substituted napthyl; pyridyl; substituted pyridyl; quinolyl; substituted quinolyl; or pentafluorobenzyl;

where the metal M is Rh, Ir, Pd, Pt, Ru, or other transition metal;

where X is Cl, Br or I; and where $R^6$ is an ancillary bidentate diene ligand selected from the group consisting of norbornene, substituted norbornene, 1,5-cyclooctadiene, and substituted 1,5-cyclooctadiene. Substituted, branched, and multiply branched substituents can be achiral, chiral, enantionmerically enriched, or racemic and substitution or branching can occur at any carbon of the base substituent. The position of substitution to a multi carbon $R^1$ group can be at any carbon containing an H in the base structure as would be recognized by one skilled in the art. Substituted can mean mono or multiply substituted where the substituent can be any alkyl, vinyl, alkenyl, alkynyl, or aryl group. Any N-heterocyclic carbene ligand can exist as a racemic mixture, as a partially or totally resolved enantiomer, or as one or more of multiple possible diastereomers.

In another embodiment of the invention the metal-carbene complex is a monometallic mono-N-heterocyclic carbene complex, as illustrated by Formula X:

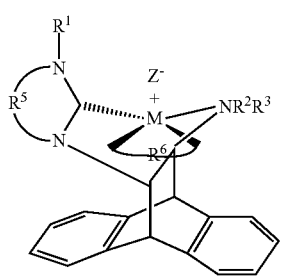

(X)

where $R^5$ is:

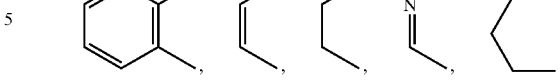

where $R^1$, $R^2$, and $R^3$ are independently: H; $C_1$ to $C_{18}$ straight, branched, or multiply branched alkyl; benzyl; substituted benzyl; phenyl; substituted phenyl; napthyl; substituted napthyl; pyridyl; substituted pyridyl; quinolyl; substituted quinolyl; or pentafluorobenzyl;

where Z is Cl$^-$, Br$^-$, PF$_6^-$, SbF$_6^-$, $^-$OSO$_2$CF$_3$, $^{-OSO}$$_2$C$_6$H$_5$ or $^-$OSO$_2$C$_6$H$_4$—R$^4$, where $R^4$ is an alkylene or oxyalkylene unit bridged with a polymer or polymeric resin;

where the metal M is Rh, Ir, Pd, Pt, Ru, or any other transition metal; and where $R^6$ is an ancillary bidentate diene ligand selected from the group consisting of norbornene, substituted norbornene, 1,5-cyclooctadiene, and substituted 1,5-cyclooctadiene. Substituted, branched, and multiply branched substituents can be achiral, chiral, enantionmerically enriched, or racemic and substitution or branching can occur at any carbon of the base substituent. The position of substitution to a multi carbon in $R^1$, $R^2$, and $R^3$ can be at any carbon containing an H in the base structure as would be recognized by one skilled in the art. Substituted can mean mono or multiply substituted where the substituent can be any alkyl, vinyl, alkenyl, alkynyl, or aryl group. Any N-heterocyclic carbene ligand can exist as a racemic mixture, as a partially or totally resolved enantiomer, or as one or more of multiple possible diastereomers.

According to an embodiment of the invention, a method to prepare the N-heterocyclic metal-carbene complex involves the combination of the N-heterocyclic carbene ligand, for example as an isolated enetetramine or bis-carbene, with a metal salt, which is typically, but not necessarily complexed with the ancillary ligand of the resulting N-heterocyclic metal-carbene complex. In another embodiment, no isolation of an N-heterocyclic carbene ligand from the reaction mixture for its formation from the N-heterocyclic carbene ligand precursor is performed, and a metal salt is added to the reaction mixture to form the N-heterocyclic metal-carbene complex.

The novel N-heterocyclic metal-carbene complexes are appropriate for use as catalyst for the following types of transformations: hydrogenation of alkenes; hydrosilation of alkenes; hydroboration of alkenes; hydroamination of alkenes; hydroformylation of alkenes; allylic alkylation; c-c coupling reactions (such as Heck, Suzuki, and Stille reactions), asymmetric aldol condensation; asymmetric diels-alder; kinetic resolution of racemic ketones, 1,4 addition of arylboronic acid to ketones; methoxycarbonylation of alkenes; CO/alkylene copolymerization; and epoxidation of alkenes. The N-heterocyclic metal-carbene complexes can promote regioselective as well as enantioselective reactions. For example, the use of a racemic N-heterocyclic metal-carbene complex will not enable the isolation of an enantionmerically enriched product when the reagents are otherwise achiral, yet can promote a regioselective reaction, for example, in an asymmetric addition to an asymmetric alkene, as in the case of a hydroformylation reaction.

The novel N-heterocyclic carbene ligands, can in themselves act as catalysts for chemical transformations initiated or promoted by carbenes. For example, the N-heterocyclic carbene ligands can be used to catalyze: [3+3] cycloadditions of enals and azomethine imines; asymmetric oxodiene diels alder reactions; benzoin condensations; Stetter reactions; Staudinger reactions; annulations of enals and unsaturated N-sulfonyl ketimines; Aza-Morita-Baylis-Hillman reactions of cyclic enones with N-tosylaryimines; ring expansion of 4-formyl-beta-lactams in syntheses of succinimide derivatives; amidations of esters with amino alcohols; epoxide ring openings; hydroacylations of ketones; and cyanosilylations.

The following examples illustrate procedures for synthesizing N-heterocyclic carbene ligand precursors, N-heterocyclic carbene ligands and N-heterocyclic metal-carbene complexes according to embodiments of the present invention.

EXAMPLES

Although methods and materials that are functionally similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the particular embodiments discussed below are illustrative only and not intended to be limiting.

Example 1

Synthesis of trans-9,10-dihydro-9,10-ethanoanthracene-11,12-di(methyltriflate)

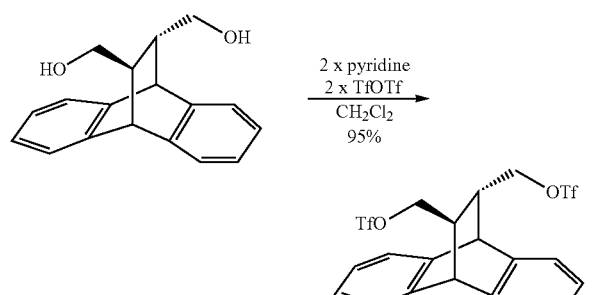

All glassware was oven-dried overnight before use. To a 250 mL round bottom with a stir bar, and pyridine (1.21 mL, 15.02 mmol) in dry methylene chloride (100 mL) was added trans-9,10-dihydro-9,10-ethanoanthracene-11,12-dimethanol (2.00 g, 7.51 mmol) at 0° C. Under argon, triflic anhydride (2.52 mL, 15.02 mmol) was added to the stirring solution through a dropping funnel over a 30 minute period. After 50 minutes the solution was washed with (3×100 mL) deionized water. The organic layer was dried over magnesium sulfate, filtered, and then evaporated under reduced pressure. The product was dried under vacuum for 1 h and then stored at −20° C. giving 3.81 g (95%) of trans-9,10-dihydro-9,10-ethanoanthracene-11,12-di(methyltriflate).

Example 2

Synthesis of trans-9,10-dihydro-9,10-ethanoanthracene-11,12-di-1-methylbenzimidazolium triflate

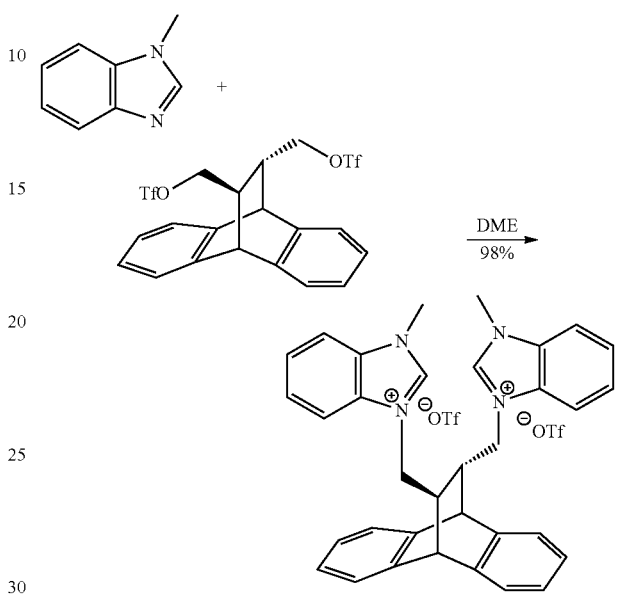

All glassware was oven-dried overnight before use. To a 100 mL round bottom with a stir bar and trans-9,10-dihydro-9,10-ethanoanthracene-11,12-dimethyltriflate (3.81 g, 7.11 mmol) in dry dimethoxyethane (30 mL) was added 1-methylbenzimidazole (1.88 g, 14.23 mmol). The reaction was stirred under argon at reflux for one hour. A white precipitate formed, which was filtered and washed with (methoxyethane giving 3.26 g (96%) of trans-9,10-dihydro-9,10-ethanoanthracene-11,12-di-1-methylbenzimidazolium triflate. The molecular structure of trans-9,10-dihydro-9,10-ethanoanthracene-11,12-di-1-methylbenzimidazolium triflate as determined by X-ray crystallography is shown in FIG. 1.

Example 3

Synthesis of trans-9,10-dihydro-9,10-ethanoanthracene-11,12-bis(1-methylbenzimidazolidine-2-ylidene

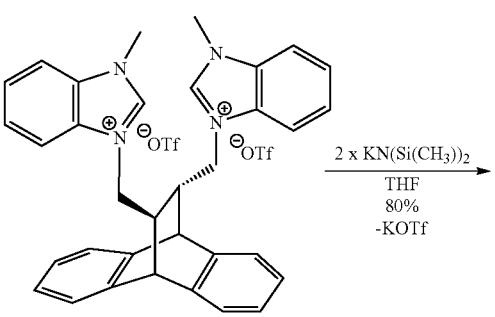

-continued

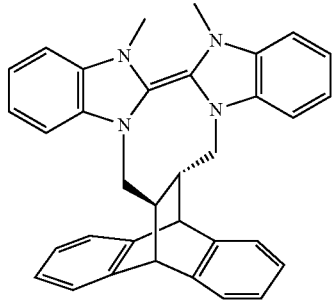

Manipulations were done in a nitrogen-filled glovebox. To a 100 mL round bottom with a stir bar and trans-9,10-dihydro-9,10-ethanoanthracene-11,12-di-1-methylbenzimidazolium triflate (1.00 g, 2.01 mmol) in THF (30 mL) was added potassium bis-trimethylsilyl amide (0.80 g, 4.03 mmol in 5 mL THF) at −25° C. The solution was stirred for an hour, and then the THF was removed under reduced pressure. The yellow solid was triturated with 5 mL of diethyl ether, followed by 2×5 mL of pentane. The yellow solid was taken up in toluene and then filter through a fine fritted funnel. The yellow material was washed with THF until a white or nearly white material was left on the fritted funnel. The filtrate is removed under reduced pressure to give 0.91 g (91%) of trans-9,10-dihydro-9,10-ethanoanthracene-11,12-bis(1-methylbenzimidazolidine-2-ylidene).

Example 4

Synthesis of Rhodium (I) trans-9,10-dihydro-9,10-ethanoanthracene-11,12-bis(1-methylbenzimidazolidine-2-ylidene norbornadiene triflate

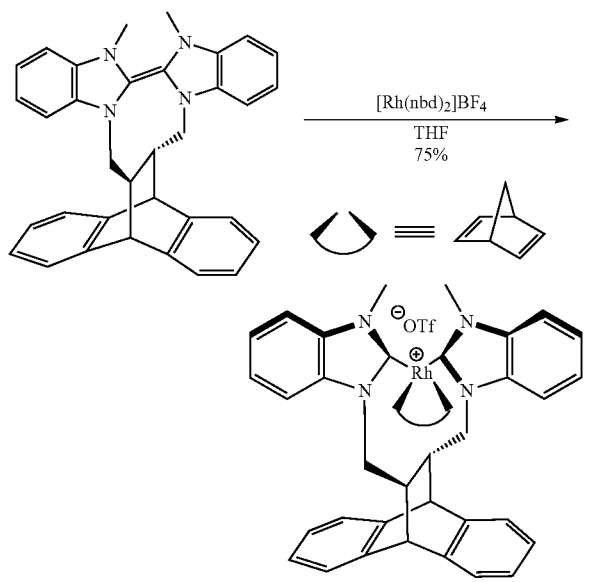

Figure 2:
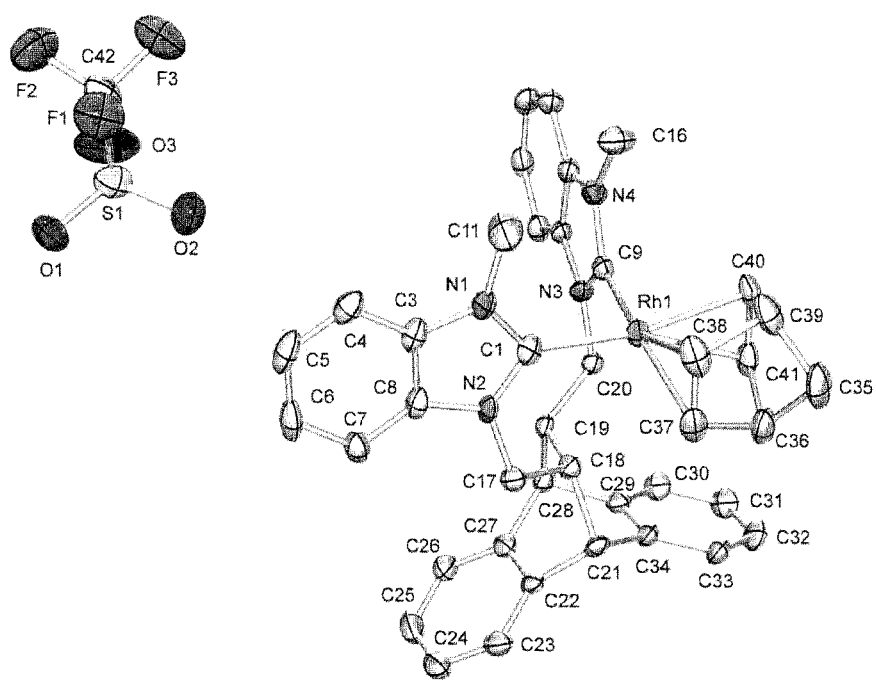
FIG. 2 shows the molecular structure of Rhodium (1) trans-9,10-dihydro-9,10-ethanoanthracene-11,12-bis(1-methylbenzimidazolidine-2-ylidene norbornadiene triflate as determined by X-ray crystallography.

Manipulations were done in a nitrogen filled glovebox. To a small glass vial with a stir bar and a solution of trans-9,10-dihydro-9,10-ethanoanthracene-11,12-bis(1-methylbenzimidazolidine-2-ylidene) (70.0 mg, 0.142 mmol in 5 mL THF) was added a solution of rhodium(I) his norbornadiene tetrafluoroborate (50.0 mg, 0.134 mmol in 5 mL THF). The reaction was stirred overnight. The yellow precipitate that formed was filtered through a fine fritted funnel and washed with 2×3 mL of cold THF to give 95 mg (97%) of Rhodium (I) trans-9,10-dihydro-9,10-ethanoanthracene-11,12-bis(1-methylbenzimidazolidine-2-ylidene norbornadiene triflate. The molecular structure of Rhodium (I) trans-9,10-dihydro-9,10-ethanoanthracene-11,12-bis(1-methylbenzimidazolidine-2-ylidene norbornadiene triflate as determined by X-ray crystallography is shown in FIG. 2.

Example 5

Synthesis of $[\mu^2\text{-DEAM-MBY}][Rh(COD)Cl]_2$

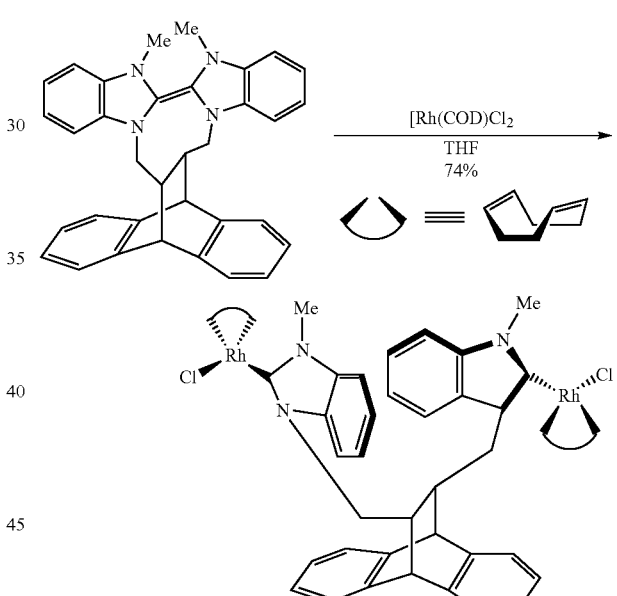

Figure 3:
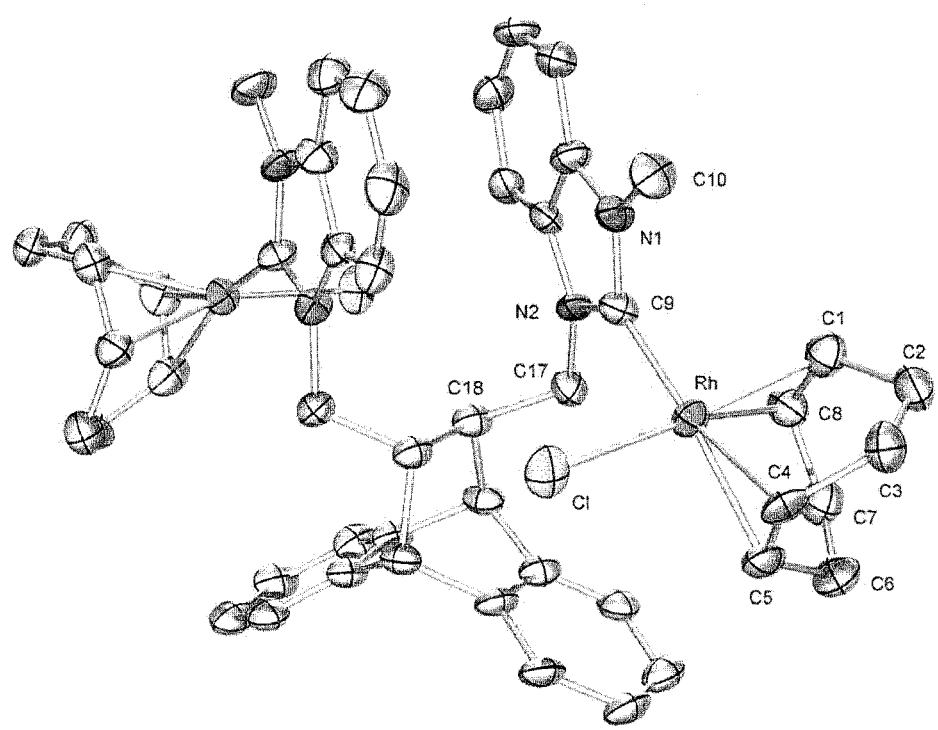
FIG. 3 shows the molecular structure of [$\mu^2$-DEAM-MBY][Rh(COD)Cl]$_2$ as determined by X-ray crystallography.

To a solution of trans-9,10-dihydro-9,10-ethanoanthracene-11,12-bis(1-methylbenzimidazolidine-2-ylidene) (33 mg, 0.067 mmol) in 3 mL THF was added a solution of $[Rh(COD)Cl]_2$ (50.1 mg, 0.134 mmol in 3 mL THF). The reaction was set aside overnight providing a yellow precipitate. The precipitate was filtered and washed with 2×3 mL of THF to provide $[\mu^2\text{-DEAM-MBY}][Rh(COD)Cl]_2$ as a yellow crystalline solid; yield 97 mg (0.05 mmol, 74%). MS (HR-ESI+): Calc. for $[C_{50}H_{54}N_4Cl_2Rh_2]$: m/z 951.2124 $[M-Cl]^+$, Found m/z 951.2106. Anal. Calc. for $C_{50}H_{54}N_4Cl_2Rh_2$: C, 60.80%; H, 5.51%; N, 5.67%. Found: C, 60.62%; H, 5.98%; N, 5.22%. The molecular structure of $[\mu^2\text{-DEAM-MBY}][Rh(COD)Cl]_2$ is shown in FIG. 3.

Example 6

Synthesis of trans-9,10-dihydro-9,10-ethanoanthracene-11,12-bis(1-isopropylbenzimidazolidine-2-ylidene)

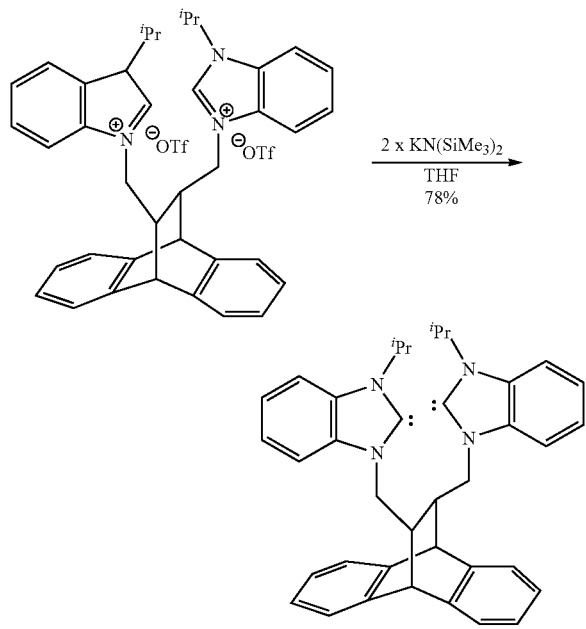

To a 100 mL flask containing a stirring bar and trans-9,10-dihydro-9,10-ethanoanthracene-11,12-di-1-isopropylbenzimidazolium triflate (1.431 g, 1.68 mmol) in THF (30 mL) was added KN(SiMe$_3$)$_2$ (0.692 g, 3.47 mmol in 5 mL THF) at −35° C. After stirring the solution for four hours, the solvent was evaporated to provide a yellow solid and a small amount of a red residue. The yellow solid was taken up in Et$_2$O, filtered, triturated with 5 mL of pentane, and then dissolved in 2 mL of THF. Additional salts were precipitated by addition of 30 mL of pentane and filtered. The filtrate was evaporated to provide trans-9,10-dihydro-9,10-ethanoanthracene-11,12-bis(1-isopropylbenzimidazolidine-2-ylidene as a pale yellow solid; yield 354 mg (0.773 mmol, 46%). $^1$H NMR (300 MHz, C$_6$D$_6$, d): 7.53 (d, J=6 Hz, 2H, NCCHCHCHCHCN), 7.10-6.88 (m, 12H, NCCHCHCHCHCN and CHCCHCH, overlapping signals), 6.81 (d, J=6 Hz, 2H, NCCHCHCHCHCN), 4.43 (sept, J=6 Hz, 2H, —CH(CH$_3$)$_2$), 4.29 (s, CCHC), 3.98 (dd, J=15 Hz, J=15 Hz, 2H, —CHH—), 3.85 (dd, J=15 Hz, J=15 Hz, 2H, —CHH—), 2.64 (dd, J=6 Hz, J=6 Hz, —CH$_2$CH), 1.56 (d, J=6 Hz, 6H, —CH(CH$_3$)$_2$), 1.51 (d, J=6 Hz, 6H, —CH(CH$_3$)$_2$). $^{13}$C NMR (75.36 MHz, C$_6$D$_6$, d): 225.59 (s, NCN), 144.50 (s, aromatic), 141.49 (s, aromatic), 136.21 (s, aromatic), 135.27 (s, aromatic), 127.33 (s, NCCHCHCHCHCN), 126.71 (s, NCCHCHCHCHCN), 126.27 (s, CHCCHCH), 123.99 (s, CHCCHCH), 121.93 (s, CHCCHCH), 121.62 (s, CHCCHCH), 110.79 (s, NCCHCHCHCHCN), 110.52 (s, NCCHCHCHCHCN), 52.74 (s, —CH$_3$), 49.84 (s, —CH(CH$_3$)$_2$), 47.31 (s, CCHC), 45.53 (s, —CH$_2$CH), 23.83 (s, —CH(CH$_3$)$_2$), 23.79 (s, —CH(CH$_3$)$_2$). GCMS (HRCI+): Calc. for C$_{38}$H$_{39}$N$_4$: m/z 551.3169 [M+H]$^+$, Found m/z 551.3218. As illustrated above in the reaction scheme, trans-9,10-dihydro-9,10-ethanoanthracene-11,12-bis(1-isopropylbenzimidazolidine-2-ylidene appears to exist as the bis-carbene in solution, as a single carbene resonance is observed downfield at 226 ppm in the $^{13}$C NMR spectrum and in the solid state as no C—C bond between the NCN carbons of the imidazoles is indicated by x-ray diffraction results.

Example 7

Synthesis of 1,1'-(9,10-dihydro-9,10-ethanoanthracene-11,12-diyl)bis(1H-imidazole) and 12-(1H-imidazol-1-yl)-9,10-dihydro-9,10-ethanoanthracen-11-amine

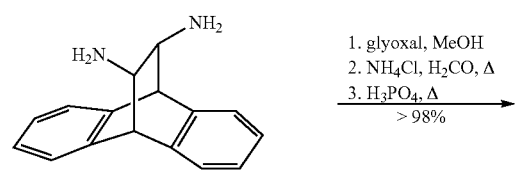

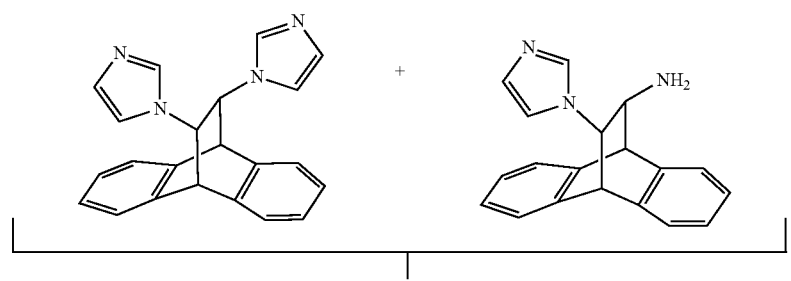

separate via chromatography

To a solution of trans-9,10-dihydro-9,10-ethanoanthracene-11,12-diamine (3.05 g, 12.9 mmol) in MeOH (20 mL) was added glyoxal (3.0 mL of 40% aqueous solution, 2 equiv, 25.8 mmol). The resulting solution turned bright yellow and became warm immediately and a light yellow precipitate formed. The mixture was stirred for 16 hours. Additional MeOH (20 mL) was added, followed by solid NH$_4$Cl (2.76 g, 4 equiv., 51.7 mmol) and HCHO (3.85 mL of 37% solution in water, 4 equiv, 51.7 mmol). The resulting mixture turned dark orange upon heated at reflux for 4 h. H$_3$PO$_4$ (3.54 mL of 85% solution in water, 4 equiv, 51.7 mL) was added slowly and the resulting mixture was heated at reflux for 16 hours. The mixture was cooled to room temperature and volatiles were removed. Dichloromethane was added and the mixture was basified to pH 14 with 10% NaOH solution. The organic extract was dried over MgSO4, filtered, and concentrated to an orange solid (3.63 g) consisting of an approximately 1:1 ratio of 1,1'-(9,10-dihydro-9,10-ethanoanthracene-11,12-diyl)bis(1H-imidazole): 12-(1H-imidazol-1-yl)-9,10-dihydro-9,10-ethanoanthracen-11-amine. 1,1'-(9,10-Dihydro-9,10-ethanoanthracene-11,12-diyl)bis(1H-imidazole) was separated from 12-(1H-imidazol-1-yl)-9,10-dihydro-9,10-ethanoanthracen-11-amine by flash column chromatography on 300 g silica gel, using 5% MeOH in CHCl$_3$ as eluent (R$_f$ of 12-(1H-imidazol-1-yl)-9,10-dihydro-9,10-ethanoanthracen-11-amine=0.28 and Rf of 1,1'-(9,10-dihydro-9,10-ethanoanthracene-11,12-diyl)bis(1H-imidazole)=0.23 in 9:1 CHCl$_3$:MeOH) to afford 1,1'-(9,10-dihydro-9,10-ethanoanthracene-11,12-diyl)bis(1H-imidazole) as a white solid (1.27 g, 30%) and 12-(1H-imidazol-1-yl)-9,10-dihydro-9,10-ethanoanthracen-11-amine as a white solid (725 mg, 20%). 1,1'-(9,10-dihydro-9,10-ethanoanthracene-11,12-diyl)bis(1H-imidazole): $^1$H NMR (300 MHz, CDCl$_3$) δ (ppm): 7.49-7.46 (m, 2H, ArH), 7.35-7.24 (m, 6H, ArH), 7.09 (dd, 2H, J=J=1.1 Hz, N—CH═NCH═CH), 6.92 (dd, 2H, J=J=1.1 Hz, N—CH═NCH═CH), 6.18 (dd, 2H, J=J=1.1 Hz, N—CH═NCH═CH) 4.50 (4H, overlapping singlets for bridge and bridgehead, CH's). $^{13}$C NMR (75.3 MHz, CDCl$_3$) δ (ppm): 140.39 (N—CH═N), 138.16 and 136.16 (C═C), 129.79 (C aromatic), 127.67 (C aromatic, overlapping signals), 126.63 (C aromatic), 124.32 (N—CH═NCH═CH), 117.10 (N—CH═NCH═CH), 64.67 (N—CH—CH—C═), 50.78 (N—CH—CH—C═). HRMS (CIP-CI) calcd (found) for C$_{22}$H$_{19}$N$_4$ (M+H)$^+$ 339.1610 (339.1649). 12-(1H-imidazol-1-yl)-9,10-dihydro-9,10-ethanoanthracen-11-amine: $^1$H NMR (300 MHz, CDCl$_3$) δ (ppm): 7.43-7.36 (m, 3H, ArH), 7.27-7.21 (m, 3H, ArH), 7.17-7.15 (m, 2H, ArH), 7.12 (dd, 1H, J=J=1.2 Hz, N—CH═N), 6.88 (dd, 1H, J=J=1.2 Hz, N—CH═NCH═CH), 6.14 (dd, 1H, J=J=1.2 Hz, N—CH═NCH═CH), 4.29 (d, 1H, J=2.4 Hz, NH$_2$CHCHN), 4.20 (d, 1H, J=2.4 Hz, NCHCH bridgehead), 3.90 (dd, 1H, J=3.6, 2.4 Hz, NH$_2$CHCHN), 3.30 (dd, 1H, J=3.7, 3.0 Hz, NH$_2$CHCH bridgehead), 1.48 (2H, NH$_2$). $^{13}$C NMR (75.3 MHz, CDCl$_3$) δ(ppm): 141.7, 140.4, 138.7 and 138.1 (C═C), 136.4 (N—CH═N), 129.1 (C aromatic), 127.03 (C aromatic), 126.9 (C aromatic), 126.8 (C aromatic), 126.7 (C aromatic), 126.5 (C aromatic), 126.2 (C aromatic), 124.1 (C aromatic), 124.04 (C aromatic), 117.7 (C aromatic), 67.4 (NH$_2$CHCHN), 60.0 (NH$_2$CHCHN), 53.3 (NCHCH bridgehead), 51.6 (NH$_2$CHCH bridgehead). HRMS (DIP-CI) calc'd (found) for C$_{19}$H$_{18}$N$_3$ (M+H)$^+$ 288.1501 (288.1496).

Example 8

Synthesis of 1,1'-(9,10-dihydro-9,10-ethanoanthracene-11,12-diyl)bis(3-methyl-1H-imidazol-3-ium) diiodide

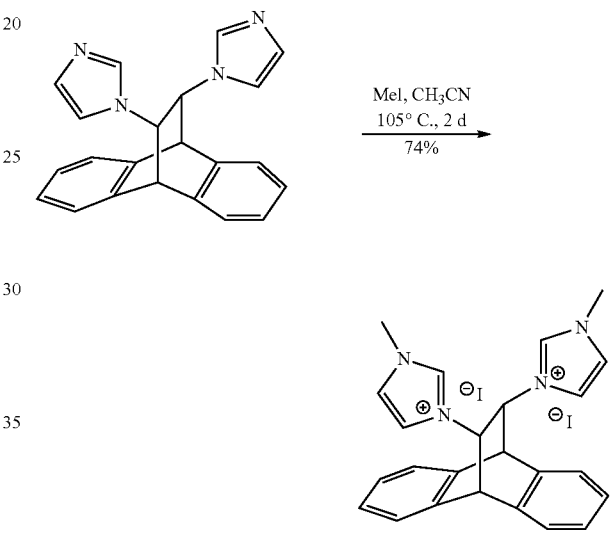

1,1'-(9,10-Dihydro-9,10-ethanoanthracene-11,12-diyl)bis(1H-imidazole) (940 mg, 2.78 mmol) was dissolved in anhydrous MeCN (15 mL) in glass ampoule fitted with a sealable Teflon stopcock. MeI (700 µL, 4 equiv, 11.1 mmol) was added and the flask was evacuated then sealed under vacuum. The flask was shielded from light and was heated in a sand bath at 105° C. for 48 hours. The mixture was cooled to room temperature and the precipitate was filtered and washed with cold MeCN to yield 1,1'-(9,10-dihydro-9,10-ethanoanthracene-11,12-diyl)bis(3-methyl-1H-imidazol-3-ium) diiodide as a beige solid (1.24 g, 72%). $^1$H NMR (300 MHz, DMSO-d$_6$) δ (ppm): 8.93 (s, 2H, N—CH═N), 7.68 (m, 2H, ImH), 7.61 (d, 2H, J=6.9 Hz, ArH), 7.41-7.35 (m, 4H, ArH), 7.30-7.25 (m, 2H, ArH), 6.60 (dd, 2H, J=J=1.5 Hz, ImH), 5.48 (s, 2H, bridge CH's), 5.05 (s, 2H, bridgehead CH's), 3.82 (s, 6H, NCH$_3$). $^{13}$C NMR (75.3 MHz, DMSO-d$_6$) δ (ppm): 139.1 and 137.3 (C═C), 136.7 (N—CH═N), 127.6 (C aromatic), 127.5 (C aromatic), 126.3 (C aromatic), 125.5 (C aromatic), 123.6 (N—CH═NCH═CH), 119.7 (N—CH═NCH═CH), 63.0 (N—CH—CH—C═), 48.3 (N—CH—CH—C═), 36.1 (NCH$_3$). HRMS (FIA-ESI) calc'd (found) for C$_{24}$H$_{24}$IN$_4$ (M-I)$^+$ 495.1040 (495.1040).

Example 9

Synthesis of Rhodium (I) trans-9,10-dihydro-9,10-ethanoanthracene-11,12-bis(1-methylbenzimidazolidine-2-ylidene) 1,5-cyclooctadiene iodide

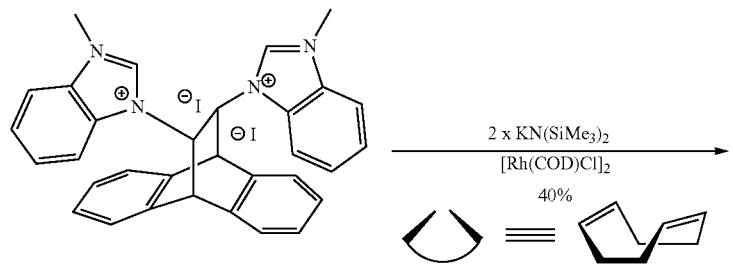

Figure 4:
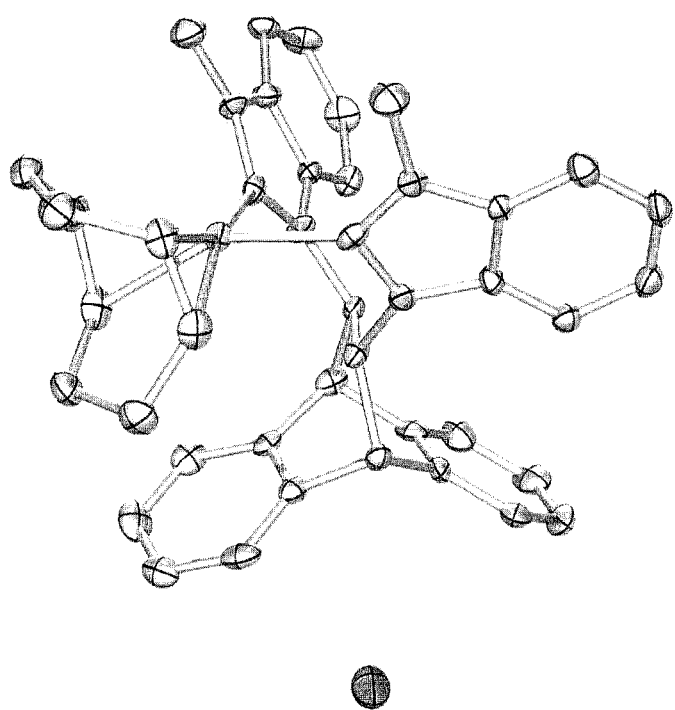
FIG. 4 shows the molecular structure of Rhodium (I) trans-9,10-dihydro-9,10-ethanoanthracene-11,12-bis(1-methylbenzimidazolidine-2-ylidene) 1,5-cyclooctadiene iodide as determined by X-ray crystallography.

KN(TMS)$_2$ (116 mg, 0.58 mmol) in 5 mL THF was added dropwise to a 5 mL solution containing 1,1'-(9,10-dihydro-9,10-ethanoanthracene-11,12-diyl)bis(1-methylbenzimidazolidine-2-ylidene) diiodide (200 mg, 0.27 mmol) and the combined solutions stirred for 2 hours. [Rh(COD)Cl]$_2$ (68 mg, 0.14 mmol in 5 mL THF) was then added dropwise to the mixture and the solution stirred for 2.5 hours. A yellow precipitate formed and was filtered and washed with ether and THF to provide Rhodium (I) trans-9,10-dihydro-9,10-ethanoanthracene-11,12-bis(1-methylbenzimidazolidine-2-ylidene 1,5-cyclooctadiene iodide as a crystalline solid; yield 90 mg, 0.12 mmol, 40%. The molecular structure of Rhodium (I) trans-9,10-dihydro-9,10-ethanoanthracene-11,12-bis(1-methylbenzimidazolidine-2-ylidene 1,5-cyclooctadiene iodide by X-ray crystallography is shown in FIG. 4.

Example 10

Regioselective Hydroformylation of Styrene

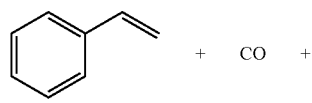
+ CO +

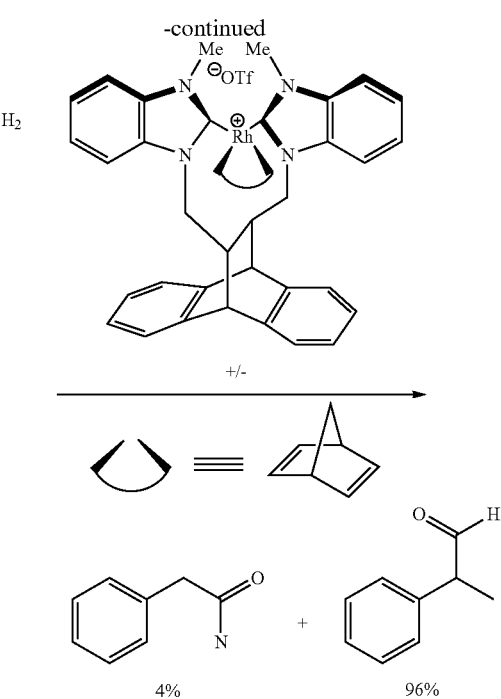

Racemic rhodium (I) trans-9,10-dihydro-9,10-ethanoanthracene-11,12-bis(1-methylbenzimidazolidine-2-ylidene norbornadiene triflate, as prepared in Example 4, was used as a catalyst to hydroformylate styrene with a 100 bar H2/CO gas atmosphere at 50° C. within 24 h. The catalyst loading was 0.01 mol %. The branched product, formed with attachment of the CO alpha to the phenyl group of styrene, was produced in 96% selective. Overall, styrene was converted nearly quantitatively to the aldehyde products. Similar results were also achieved for the hydroformylation of allycyanide and vinyl acetate as indicated in Table 1 below with high regioselectivity and essentially quantitative hydroformylation.

TABLE 1

Hydroformylation of Alkenes

| Substrate | mol % catalyst | $H_2$/CO | time (h) | % conversion | % branched isomer |
|---|---|---|---|---|---|
| 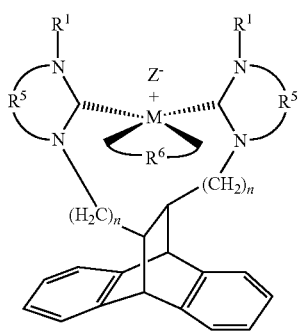 | 01 | 100 | 24 | >99 | 96 |
| | 0.1 | 100 | 24 | >99 | 75 |
| | 0.1 | 100 | 24 | >99 | 96 |

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A monometallic bis-N-heterocyclic carbene complex, comprising a structure of Formula VIII:

(VIII)

wherein n is 0 or 1;
wherein $R^5$ is independently:

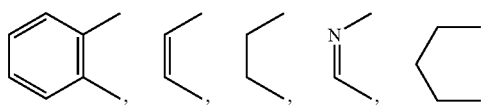

wherein $R^1$, groups are independently: H; $C_1$ to $C_{18}$ straight, branched, or multiply branched alkyl; benzyl; substituted benzyl; phenyl; substituted phenyl; naphthyl; substituted naphthyl; pyridyl; substituted pyridyl; quinolyl; substituted quinolyl; or pentafluorobenzyl, wherein the substituent is an alkyl, vinyl, alkenyl, alkynyl, or aryl group;
wherein Z is $Cl^-$, $Br^-$, $I^-$, $PF_6^-$, $SbF_6^-$, $^-OSO_2CF_3$, $^-OSO_2C_6H_5$ or $^-OSO_2C_6H_4$—$R^4$ where $R^4$ is an alkylene or oxyalkylene unit bridged with a polymer or polymeric resin;
wherein M is Rh, Ir, Pd, Pt, Ru, or other transition metal; and
wherein a second ligand, $R^6$, is: norbornene; substituted norbornene; 1,5-cyclooctadiene; or substituted 1,5-cyclooctadiene, wherein the substituent is an alkyl, vinyl, alkenyl, alkynyl, or aryl group.

2. The monometallic bis-N-heterocyclic carbene complex of claim 1, wherein n is 1, $R^5$ is

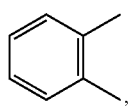

and M is Rh.

3. The monometallic bis-N-heterocyclic carbene complex of claim 1,
wherein n is 0, $R^5$ is

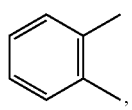

and M is Rh.

4. A bimetallic bis-N-heterocyclic carbene complex, comprising a structure of Formula IX:

(IX)

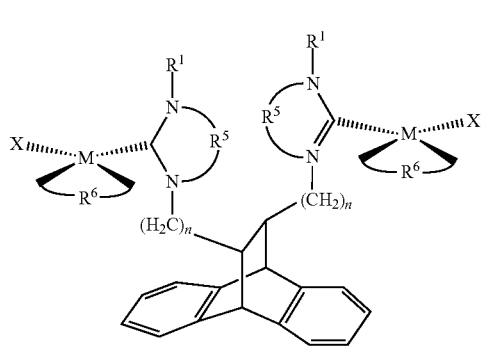

wherein n is 0 or 1;
wherein $R^5$ is independently:

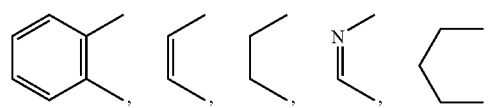

wherein $R^1$, $R^2$, and $R^3$ groups are independently: H; $C_1$ to $C_{18}$ straight, branched, or multiply branched alkyl; benzyl; substituted benzyl; phenyl; substituted phenyl; naphthyl; substituted naphthyl; pyridyl; substituted pyridyl; quinolyl; substituted quinolyl; or pentafluorobenzyl, wherein the substituent is an alkyl, vinyl, alkenyl, alkynyl, or aryl group;

wherein M is Rh, Ir, Pd, Pt, Ru, or other transition metal;
wherein anion X is Cl, Br or I; and
wherein a second ligand, $R^6$, is norbornene; substituted norbornene; 1,5-cyclooctadiene; or substituted 1,5-cyclooctadiene, wherein the substituent is an alkyl, vinyl, alkenyl, alkynyl, or aryl group.

5. A monometallic mono-N-heterocyclic carbene complex, comprising a structure of Formula X:

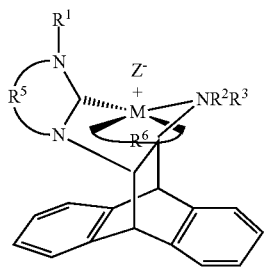
(X)

wherein $R^5$ is:

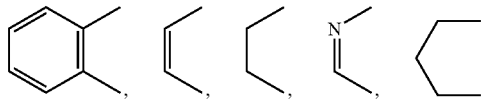

wherein $R^1$, $R^2$, and $R^3$ are independently: H; $C_1$ to $C_{18}$ straight, branched, or multiply branched alkyl; benzyl; substituted benzyl; phenyl; substituted phenyl; naphthyl; substituted naphthyl; pyridyl; substituted pyridyl; quinolyl; substituted quinolyl; or pentafluorobenzyl, wherein the substituent is an alkyl, vinyl, alkenyl, alkynyl, or aryl group;
wherein Z is $Cl^-$, $Br^-$, $I^-$, $PF_6^-$, $SbF_6^-$, $^-OSO_2CF_3$, $^-OSO_2C_6H_5$ or $^-OSO_2C_6H_4$—$R^4$ where $R^4$ is an alkylene or oxyalkylene unit bridged with a polymer or polymeric resin;
wherein the metal M is Rh, Ir, Pd, Pt, Ru, or any other transition metal; and
wherein a second ligand, $R^6$, is norbornene; substituted norbornene; 1,5-cyclooctadiene; or substituted 1,5-cyclooctadiene, wherein the substituent is an alkyl, vinyl, alkenyl, alkynyl, or aryl group.

6. A method of preparing a monometallic bis-N-heterocyclic metal-carbene complex comprising combining an N-heterocyclic carbene ligand with a metal salt and a second ligand, wherein the bis-N-heterocyclic carbene ligand is

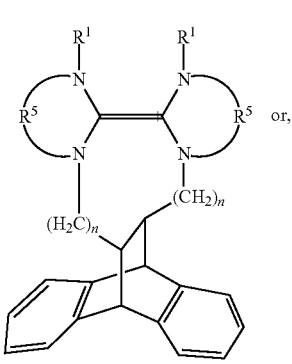
(V)

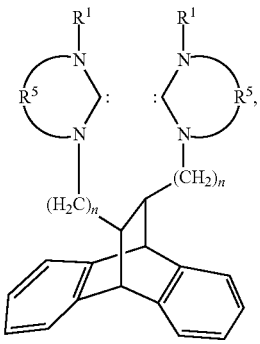
(VI)

wherein: n is 0 or 1;
wherein $R^5$ is independently:

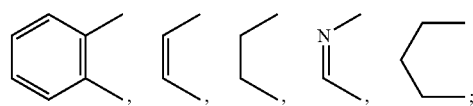

and
wherein $R^1$ groups are independently: H; $C_1$ to $C_{18}$ straight, branched, or multiply branched alkyl; benzyl; substituted benzyl; phenyl; substituted phenyl; naphthyl; substituted naphthyl;
pyridyl; substituted pyridyl; quinolyl; substituted quinolyl; or pentafluorobenzyl, wherein the substituent is an alkyl, vinyl, alkenyl, alkynyl, or aryl group, wherein the metal salt comprising a metal and an anion, wherein the metal is Rh, Ir, Pd, Pt, Ru, or other transition metal, the anion is $Cl^-$, $Br^-$, $I^-$, $PF_6^-$, $^-OSO_2CF_3$, $^-OSO_2C_6H_5$ or $^-OSO_2C_6H_4$—$R^4$, where $R^4$ is an alkylene or oxyalkylene unit bridged with a polymer or polymeric resin, and wherein the second ligand is norbornene; substituted norbornene; 1,5-cyclooctadiene; or substituted 1,5-cyclooctadiene, wherein the substituent is an alkyl, vinyl, alkenyl, alkynyl, or aryl group.

7. The method of claim 6, wherein said N-heterocyclic carbene ligand is of Formula V or Formula VI and said metal complex is $[Rh(COD)Cl]_2$ or rhodium(I) bis-norbornadiene tetrafluoroborate.

8. A method of preparing bimetallic bis-N-heterocyclic metal-carbene complex comprising combining a bis-N-heterocyclic carbene ligand with a metal salt and a second ligand, wherein the bis-N-heterocyclic carbene ligand is

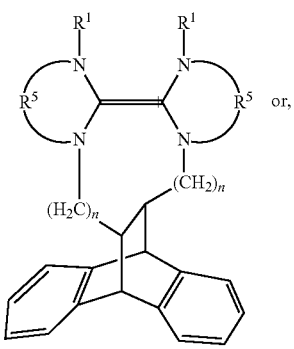
(V)

-continued (VI)

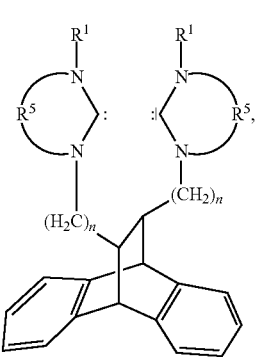

wherein: n is 0 or 1;
wherein $R^5$ is independently:

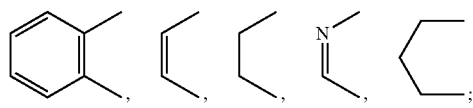

and
wherein $R^1$ groups are independently: H; $C^1$ to $C^{18}$ straight, branched, or multiply branched alkyl; benzyl; substituted benzyl; phenyl; substituted phenyl; naphthyl; substituted naphthyl; pyridyl; substituted pyridyl; quinolyl; substituted quinolyl; or pentafluorobenzyl, wherein the substituent is an alkyl, vinyl, alkenyl, alkynyl, or aryl group, at least one metal salt wherein the metal salt comprises a metal and an anion, where the metal is Rh, Ir, Pd, Pt, Ru, or other transition metal and the anion is $Cl^-$, $Br^-$, $I^-$, $PF_6^-$, $SbF_6^-$, $^-OSO_2CF_3$, $^-OSO_2C_6H_5$ or $^-OSO_2C_6H_4-R^4$, where $R^4$ is an alkylene or oxyalkylene unit bridged with a polymer or polymeric resin, and the second ligand is: norbornene, substituted norbornene; 1,5-cyclooctadiene; or substituted 1,5-cyclooctadiene, wherein the substituent is an alkyl, vinyl, alkenyl, alkynyl, or aryl group.

9. A method of preparing a monometallic mono-N-heterocyclic carbene complex comprising combining a mono-N-heterocyclic carbene ligand with a metal salt and a second ligand, wherein the mono-N-heterocyclic carbene ligand comprises an N-heterocyclic carbene ligand, a metal, a second ligand and an anion, wherein the N-heterocyclic carbene ligand is (VII)

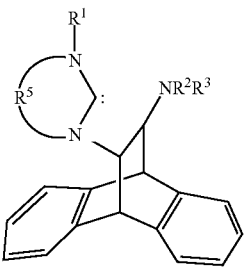

wherein $R^5$ is:

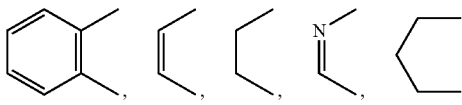

wherein $R^1$, $R^2$, and $R^3$ are independently: H; $C_1$ to $C_{18}$ straight, branched, or multiply branched alkyl; benzyl; substituted benzyl; phenyl; substituted phenyl; naphthyl; substituted naphthyl; pyridyl; substituted pyridyl; quinolyl; substituted quinolyl; or pentafluorobenzyl, wherein the substituent is an alkyl, vinyl, alkenyl, alkynyl, or aryl group, the metal salt comprises a metal and an anion, where the metal is Rh, Ir, Pd, Pt, Ru, or other transition metal and the anion is $Cl^-$, $Br^-$, $I^-$, $PF_6^-$, $SbF_6^-$, $^-OSO_2CF_3$, $^-OSO_2C_6H_5$ or $^-OSO_2C_6H_4-R^4$, where $R^4$ is an alkylene or oxyalkylene unit bridged with a polymer or polymeric resin, and the second ligand is norbornene; substituted norbornene; 1,5-cyclooctadiene; or substituted 1,5-cyclooctadiene, wherein the substituent is an alkyl, vinyl, alkenyl, alkynyl, or aryl group.

* * * * *

UNITED STATES PATENT AND TRADEMARK OFFICE
CERTIFICATE OF CORRECTION

PATENT NO. : 8,455,661 B2
APPLICATION NO. : 12/527635
DATED : June 4, 2013
INVENTOR(S) : Adam Steven Veige et al.

It is certified that error appears in the above-identified patent and that said Letters Patent is hereby corrected as shown below:

In the Specification:

Column 2,
Lines 31-32, "method involve" should read -- method involves --.
Line 41, "his-carbene" should read -- *bis*-carbene --.
Line 42, "his-carbene" should read -- *bis*-carbene --.

Column 4,
Line 65, "his-N-heterocyclic" should read -- *bis*-N-heterocyclic --.

Column 5,
Line 41, "resin" should read -- resin. --.

Column 7,
Line 34, "introducing one" should read -- introducing of one --.

Column 12,
Line 15, "$^{-OSO}{}_2C_6H_5$ or" should read -- $^-OSO_2C_6H_5$ or --.

Column 16,
Line 5, "his norbornadiene" should read -- *bis* norbornadiene --.
Line 30, "[Rh(COD)Cl$_2$" should read -- [Rh(COD)Cl]$_2$ --.

Signed and Sealed this
Eighth Day of October, 2013

Teresa Stanek Rea
*Deputy Director of the United States Patent and Trademark Office*

Column 16,
Lines 39-41,
" 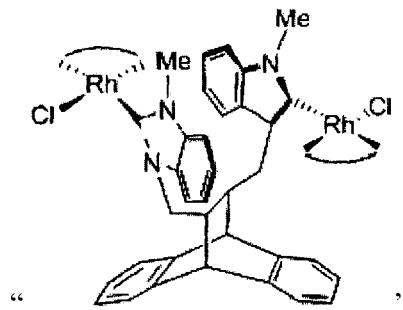 " should read -- 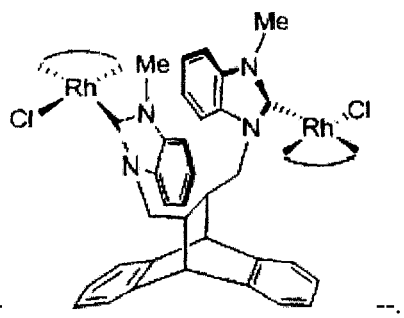 --.
Column 17,
Lines 9-10,
" 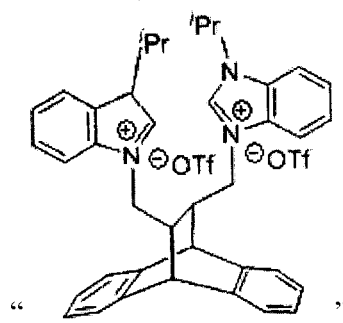 " should read -- 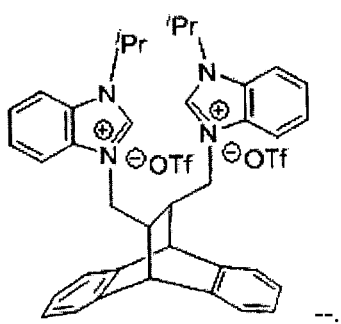 --.
Column 18,
Lines 36-37, "ethanoanthracen-11-amine" should read -- ethanoanthracene-11-amine --.
Column 22,
Lines 59-61,
" 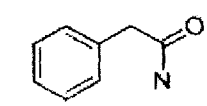 4 % " should read -- 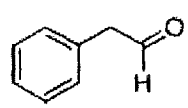 4 % --.
Column 23,
Line 18, "01" should read -- 0.1 --.